US006654445B2

(12) United States Patent
Shepherd et al.

(10) Patent No.: US 6,654,445 B2
(45) Date of Patent: *Nov. 25, 2003

(54) DEVICE AND METHOD FOR DETERMINING PROPORTIONS OF BODY MATERIALS

(75) Inventors: John A. Shepherd, Novato, CA (US); Steven R. Cummings, Mill Valley, CA (US); Karla Kerlikowske, San Alselmo, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/302,683

(22) Filed: Nov. 22, 2002

(65) Prior Publication Data

US 2003/0142780 A1 Jul. 31, 2003

Related U.S. Application Data

(63) Continuation of application No. 09/848,922, filed on May 4, 2001, now Pat. No. 6,516,045.

(51) Int. Cl.[7] ............................. G61J 23/06; A61B 6/04
(52) U.S. Cl. ......................... 378/53; 378/56; 378/207; 382/132
(58) Field of Search .............................. 378/37, 53, 54, 378/56, 62, 207; 382/132, 171, 173

(56) References Cited

U.S. PATENT DOCUMENTS

| 5,142,557 | A |   | 8/1992  | Toker et al. ................... 378/37  |
| 5,657,362 | A |   | 8/1997  | Giger et al. ................... 378/37  |
| 5,768,334 | A |   | 6/1998  | Maitrejean et al. ........... 378/53  |
| 5,933,578 | A |   | 8/1999  | Van de Capelle et al. .. 382/132 |
| 6,009,147 | A |   | 12/1999 | Stein et al. .................. 378/196 |
| 6,173,038 | B1 |  | 1/2001  | Siffert et al. ................... 378/56 |
| 6,292,535 | B1 | * | 9/2001  | Williams et al. ............ 378/98.8 |
| 6,320,931 | B1 |  | 11/2001 | Arnold ......................... 378/56 |
| 6,430,252 | B2 |  | 8/2002  | Reinwand et al. ............. 378/8 |
| 6,516,045 | B2 | * | 2/2003  | Shepherd et al. ............. 378/53 |

OTHER PUBLICATIONS

SJ Graham, MJ Bronskill, JW Byng, MJ Yaffe and NF Boyd; "Quantitative correlation of breast tissue parameters using magnetic resonance and X–ray mammography;" British Journal of Cancer (1996) 73, 162–168.
Prudence B. Lam, Pamela M. Vacek, Berta M. Geller, Hyman B. Muss; "The association of increased weight, body mass index, and tissue density with the risk of breast carcinoma in Vermont;" Cancer Jul. 15, 2000/vol. 89/No. 2.
Margaer T. Mandelson, Nina Oestreicher, Peggy L. Porter, Donna White, Charles A. Finder, Stephen H. Taplin, Emily White; "Breast density as a predictor of mammographic detection: comparison of interval–and screen–detected cancers;" Journal of the National Cancer Institute. vol. 92, No. 13, Jul. 5, 2000.
HW Wahner, P Steiger and Eric Von Stetten; "The evaluation of osteoporosis: Dual energy X–ray absorptiometry in clinical practice," Chapter 3, "Instruments and measurement techniques."
MJ Yaffe, NF Boyd, JW Byng, RA Jong, E. Fishell, GA Lockwood, LE Little, D1 Tritchler; "Breast cancer risk and measured mammographic density;" European Journal of Cancer Prevention 1998, 7 (suppl 1): S47–S55.

* cited by examiner

*Primary Examiner*—Drew A. Dunn
(74) *Attorney, Agent, or Firm*—Lumen Intellectual Property Services, Inc.

(57) ABSTRACT

The present invention provides a radiation device that includes a device for retaining therein the body part in a uniform position. In addition, at least two reference materials that have attenuation characteristics are used and retained in the retaining device. The reference materials are being positioned for the comparative determination during a simultaneous irradiation of the body part and the reference materials. The attenuation characteristics of the reference materials are selected in correspondence to the attenuation characteristics of the body materials in the body part. A radiation device for simultaneously irradiating the body part and the reference materials is used to create attenuated beams. A detector is used to detect the attenuated beams as attenuated values. A calculating device is included for calculating the proportion of the body materials that define a particular body part of interest based on the attenuated values of the materials and the body part.

66 Claims, 4 Drawing Sheets

DEVICE AND METHOD FOR DETERMINING PROPORTIONS OF BODY MATERIALS

REFERENCE TO RELATED APPLICATIONS

This application is continuation of parent application Ser. No. 09/848,922 filed on e May 4, 2001 now U.S. Pat. No. 6,516,045.

STATEMENT REGARDING FEDERALLY SPONSORED RESEARCH OR DEVELOPMENT

This invention was supported in part by grant number BC99540 from the Department of the Army Medical Research Division. The U.S. Government has certain rights in the invention.

FIELD OF THE INVENTION

This invention relates generally to radiography. More particularly, the present invention relates to a device and method for measuring proportions of body materials in body parts of humans and animals.

BACKGROUND

The determination of proportions or densities of different body materials in body parts of humans or animals is of utmost importance to monitor, for instance, cancer risk in clinical drug trials, epidemiological studies, or routine screening. The measures of proportions or densities could be shown to be useful as markers to predict, for instance, breast cancer risk and possibly risk of disease recurrence or change in breast cancer risk.

In order to obtain these measures, techniques have been developed to maximize the radiographic contrast of tissue composition of a body part to better discriminate cancer risk. The x-ray energies, dose levels, and film/screen combinations are typically designed to maximize the radiographic tissue composition contrast. As an example, breast density was initially described using a semi-quantitative classification system that took into account the quantitative (amount of density) and qualitative nature of the density (diffuse or associated with ductal structures). Four to ten category systems have been previously used to cover the entire density range. A more quantitative approach measures the area of mammographically dense breast area relative to the total projected breast area, referred to as mammographic density. Mammographic density is a quantitative continuous grading from 0 to 100% density measured by delineating the radiographically dense areas in the mammogram from the entire breast area and providing a percentage breast density. Although mammographic density is currently a widely used technique, it has serious limitations. First, since the films are uncalibrated for mass density versus film optical density, a unique threshold has to be picked for each film. The total and dense projected areas will change based on the amount of compression. For example, in a typical laboratory, the reproducibility of delineating the dense regions by an expert radiologist on the same image is approximately 5–7%. If both delineation errors and patient repositioning errors are conservatively assumed to be 7%, the 95% confidence for a significant change in density is approximately 14%. Thus, the sensitivity for risk classification and change in follow-up examinations is similar to that of the categorical methods.

There are many competing methods readily available to estimate body fat but only a few, Dual Energy X-ray Absorptiometry (DXA), Computed Tomography (CT) and Magnetic Resonance Imaging (MRI) are capable of measuring the tissue composition of specific compartments of the body. CT and MRI work by segmenting the fat from the lean tissue components for individual image planes. Summing all the slices of a whole breast scan to form a volume results in a whole organ % fat mass. The whole organ radiation dose of CT limits its usefulness as a screening tool. The overall costs and availability of both CT and MR further limit their practicality as a screening tool. For these reasons and its very high precision (~300 grams for human whole body measurements and <50 g in small animals), DXA body composition measurements are the clinical standard for whole body and subregional compositional measurements. DXA measurements are low dose, typically less than 5 μSv for any procedure, but require the acquisition of two images with beam hardening on the higher energy image. Prior to the development of DXA, Single Energy X-ray Absorptiometry (SXA) was used to measure bone density in peripheral bone site such as the forearm. For instance, a forearm was submerged in water such that the soft tissue in water provided uniform background attenuation. This technique eliminated the problem of soft tissue thickness variation and the bone attenuation was then simply the attenuation values above a water/soft tissue threshold.

Accordingly there is a need to develop a more practical device and method to quantify proportions or densities of different body materials in body parts of humans and animals.

SUMMARY OF THE INVENTION

This invention provides generally a radiography device and method. More particularly, the present invention provides a device and method for measuring proportions of body materials in body parts of humans and animals. The device and method enables one to determine a proportion of body materials in body parts of interest in, for instance, clinical drug trials and epidemiological cancer risk studies. Measures of body part proportions could be useful as a marker to predict cancer risk and possibly risk of disease recurrence or change in cancer risk. Furthermore, classification of cancer types could be improved with the device and method of the present invention since it provides for a more reproducible and more sensitive approach.

In accordance with exemplary embodiments of the present invention, a radiation device is provided for comparatively determining a proportion of body materials that define a body part. A more detailed embodiment is provided wherein breast density, as the proportion of body materials of a breast is determined. The present invention is, however, not restricted to the use of a breast and could also include other body parts of the human and animal body. The radiation device includes a device for retaining therein the body part in a uniform position. In addition, at least two reference materials that have attenuation characteristics are used. These reference materials are also retained in the retaining device. In the example of the breast, the reference materials represent for instance fat and lean tissue. However, the present invention is not limited to the choice of these materials or to the selection of only two materials. The breast could also be modeled as having three or more different materials. The reference materials are being positioned in the retaining device for the comparative determination during a simultaneous irradiation of the body part and the reference materials. The attenuation characteristics of the reference materials are selected in correspondence to the attenuation characteristics of the body materials in the body part. A radiation means for simultaneously irradiating the body part and the reference materials is used to create attenuated beams of the materials and the body part. A detector is used to detect and present the attenuated beams as attenuated values of the materials and the body part. A calculating means, such as a computer, is included for calculating the proportion of the body materials that define a particular body part of interest based on the attenuated values of the materials and the body part.

In view of that which is state above, it is the objective of the present invention to provide a device and method that determines a proportion of body materials as in for instance a fat and lean ratio of a breast. It is another objective of the present invention to provide a method and device to predict cancer risk and monitor drug trials. The advantage of the present invention is that the results obtained by using the device and method are irrespective of patient's repositioning errors and reproducible. The device and method are also sensitive in determining the proportions of body materials. In addition, the device and method of the present invention does not require additional calibration. Finally, the present invention uses just one image of the body part of interest. This enables one to use radiation techniques such as single energy X-ray absorptiometry as well as single photon absorptiometry. Therefore an additional advantage is that the use of the present invention reduces the amount of radiation exposure.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiments of the invention is set forth without any loss of generality to, and without imposing limitations upon, the claimed invention.

The present invention involves a device and method that enables one to determine a proportion of body materials in body parts of interest in, for instance, clinical drug trials and epidemiological cancer risk studies. Measures of body part proportions could be useful as a marker to predict cancer risk and possibly risk of disease recurrence or change in cancer risk. For example, promising interventions that may decrease breast cancer risk such as a low fat diet, phytoestrogens or hormone manipulations could be first tested by examining whether the proportion of breast area with mammographic densities is affected by the intervention prior to conducting a large randomized controlled trial that determines the influence on breast cancer incidence. Breast density could also be used to identify women at sufficient risk to warrant treatment with SERMS or new agents for prevention of breast cancer. The present invention could also provide a new device and method for clinical and basic scientists to better understand how proliferated breast stroma (mammographic breast densities) may interact with breast epithelium to promote growth of breast tumor cells.

Furthermore, classification of breast cancer types could be improved with the device and method of the present invention since it provides for a more reproducible and more sensitive approach. It is irrespective of patient repositioning errors and does not need additional calibration.

Figure 1:
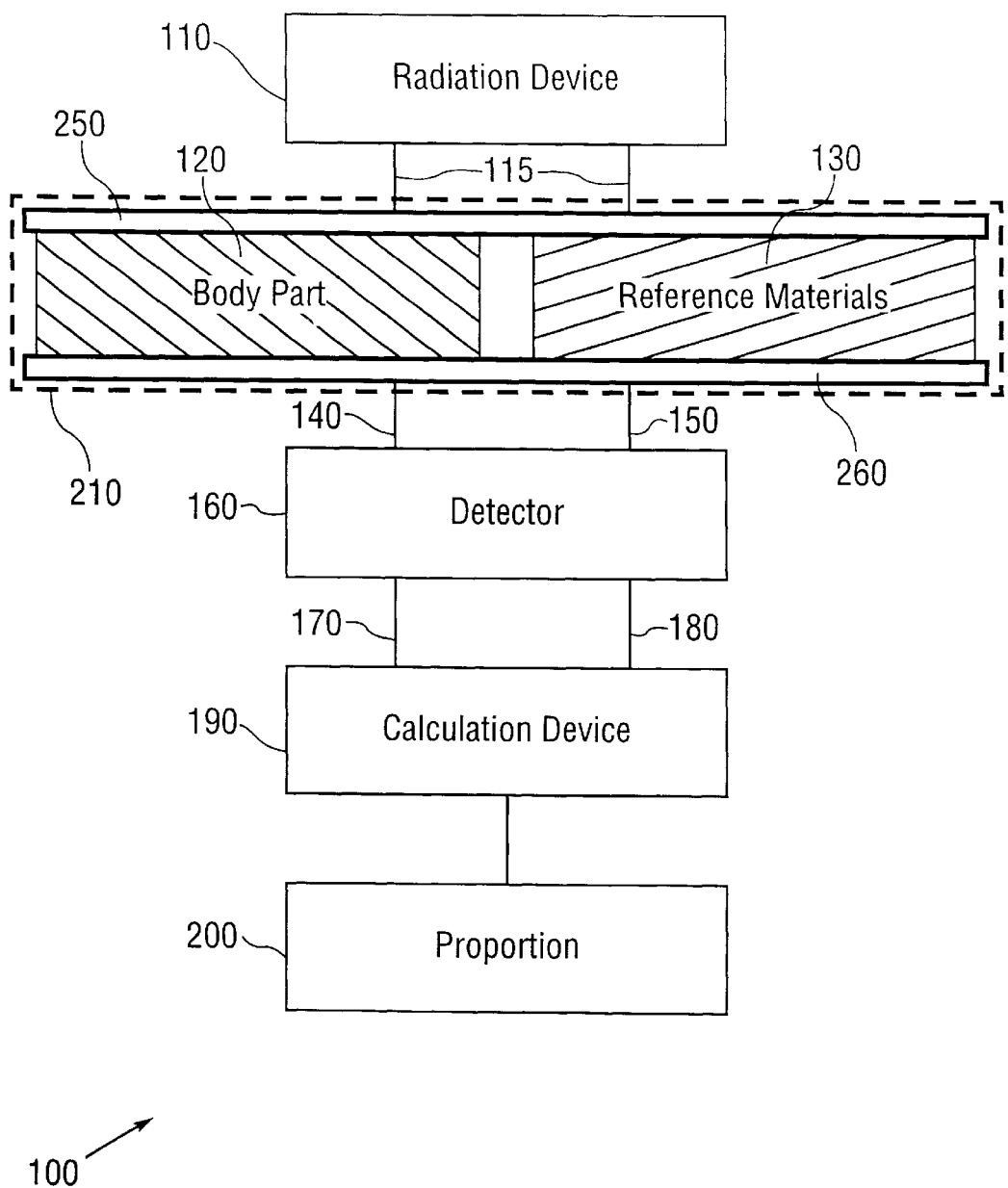
FIG. 1 illustrates the general concept of a radiation device and method according to the present invention.

FIG. 1 shows a simplified flow diagram of the radiation device 100 according to the present invention that involves the comparative determination of a proportion of body materials 200 defining a body part 120. The present invention involves the determination of a proportion 200 of, for instance, fat and glandular tissue in a breast. The present invention is not limited to the determination of just two materials as it can also, for instance, include materials such as muscle tissue, skin tissue, organ tissue, bone tissue, or the like. The choice of the particular body part 120 of interest is extensive, and not just limited to a breast. For instance, one can think of different parts of extremities such as an ear, a tongue, a testicle, skin folds or body parts that include a particular organ such as a liver or kidney. The key idea behind the present invention is that a body part 120 is modeled having at least two different materials, such as fat tissue and lean tissue in a breast. In general, the part could include a part from a human, animal or a plant. Furthermore, the part of the present invention could include processed tissue or meat (e.g. grounded beef) or a homogenized tissue.

The present invention requires one to select at least two reference materials 130 having attenuation characteristics. The selection of the reference materials 130 is such that the attenuation characteristics are in correspondence to the type of body materials as they are modeled in the body part 120 of interest. In the case of fat and lean tissue of the breast, the selection could then be two reference materials 130 having corresponding attenuation characteristics to fat and lean. The selection of the number of materials 130 depends on the type of examination or study as well as the level of detail or type of material that is of interest to a physician, scientist or epidemiologist.

FIG. 1 also shows a radiation means 110 that simultaneously irradiates the body part and the reference materials with beams 115. After passing through the body part and reference materials, the beams 115 are attenuated beams 140 and 150 of the body part 120 and the reference materials 130 respectively. The radiation source 110 provides a simultaneous radiation in order to provide a single image of the body part and reference material. In that respect the radiation source 110 could for instance be a single energy X-ray absorptiometer (SXA) or a single photon absorptiometer (SPA). The use of just a single image by means of for instance SXA or SPA results in a reduction of the total amount of radiation exposure to a body part. Other techniques than SXA or SPA to provide a simultaneous radiation are also possible.

The radiation device 100 also includes a detector 160 to detect the attenuated beams 140 and 150 as attenuated values 170 and 180 of respectively the body part and reference materials. Preferably, the detector 160 detects the attenuated values 170 and 180 as a single image, but is not limited to a single image since it could also be multiple images as long as the attenuated values 170 and 180 are available for comparison. The detector 160 provides, for instance, a film or a screen to make an image of the attenuated beams 140 and 150, or a digital device that acquires the attenuated beams 140 and 150 and convert those into digital values. The detector 160 also includes means for presenting or recording the attenuated values 170 and 180 in, for instance, a color scheme or a gray scale. The idea behind the detector 160 is to provide a continuous scale with a large enough resolution for the attenuation values to identify the selected materials in body part 120. Discrete scales are also possible.

The attenuation values 180 of the reference materials 130 are used as a reference or calibration for the attenuation values 170 of the body part 120 of interest to calculate or determine the proportion 200 of selected body materials. For instance, a comparison can be made between the percentage fat and lean tissue of a breast provided that the attenuation values of the breast can be compared with the attenuation values of the fat reference material and lean reference material.

Figure 2:
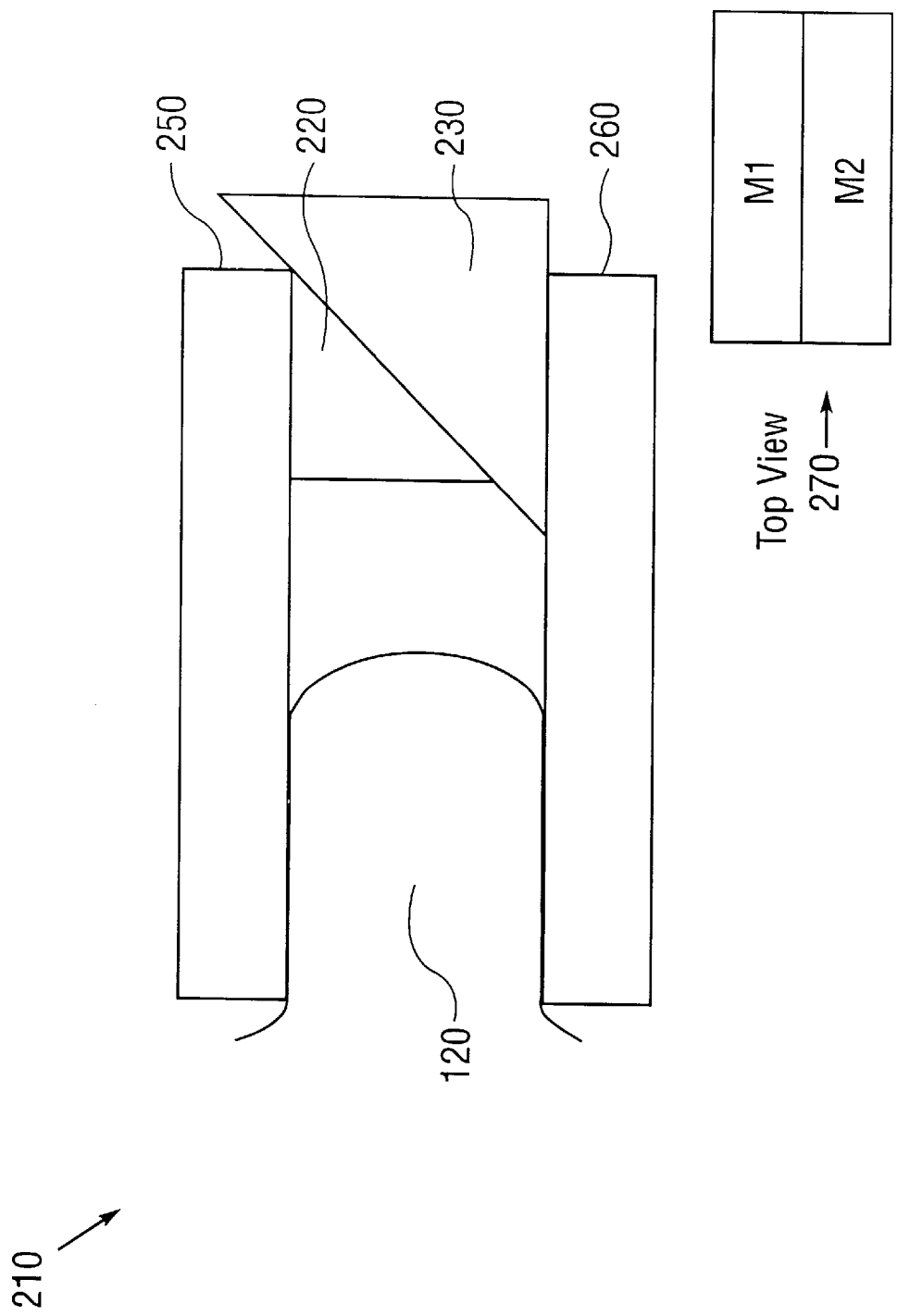
FIGS. 2-4 illustrates three embodiments of a retaining device and method according to the present invention.
Figure 3:
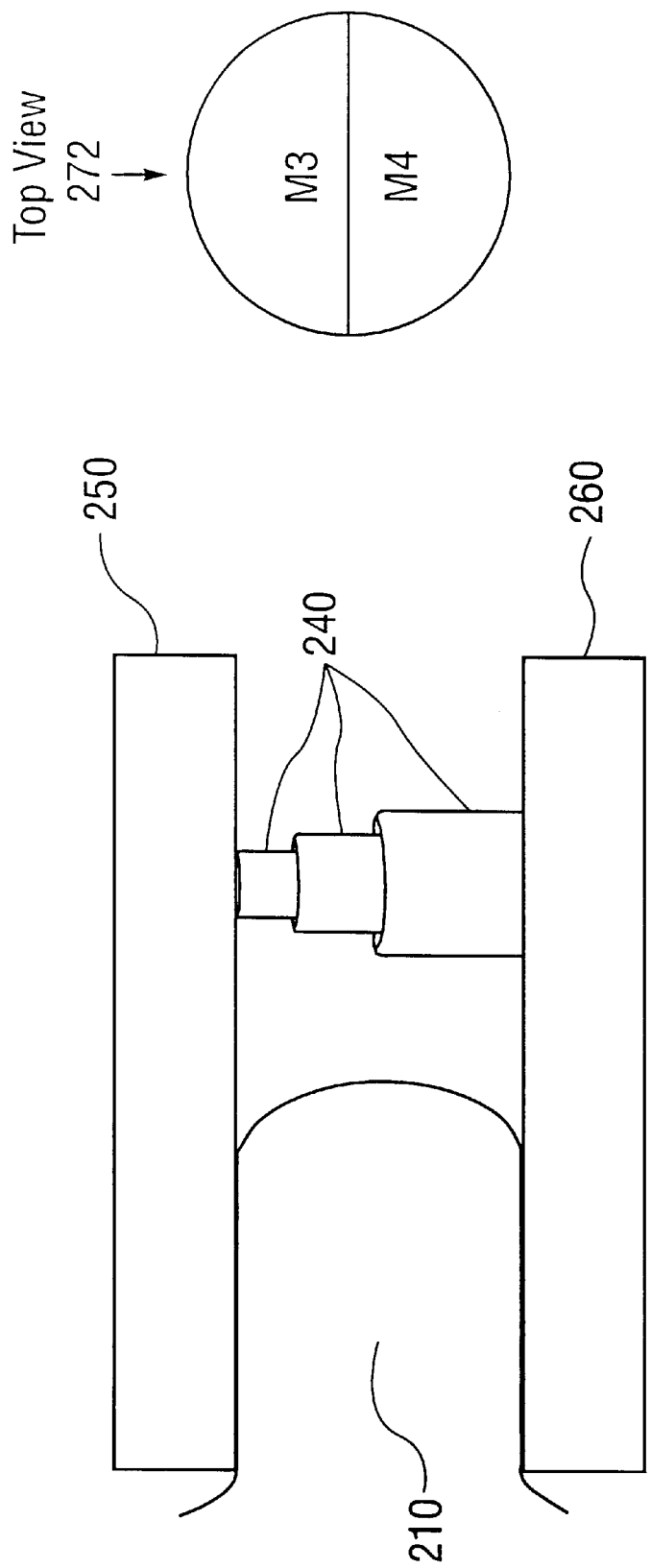
Figure 4:
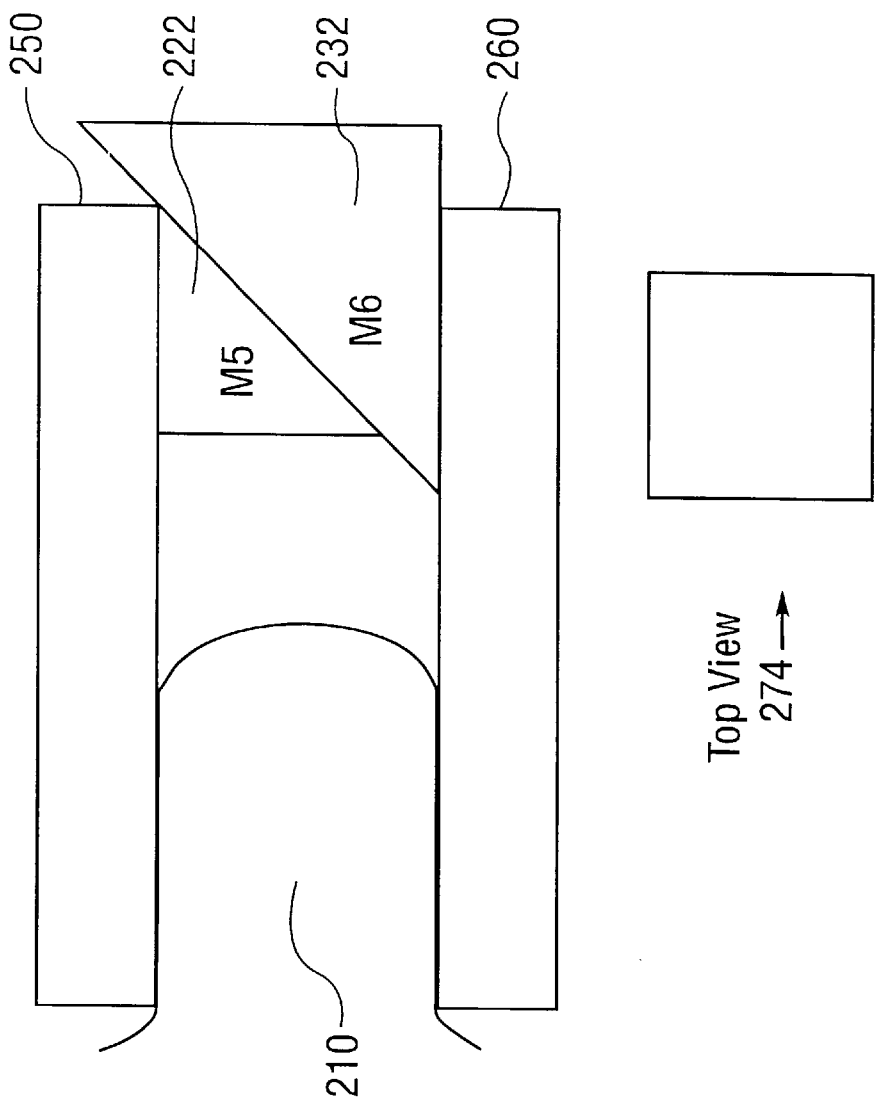

FIG. 1 shows a retaining device 210, as part of the radiation device 100, which is shown in more detail in FIGS. 2, 3 and 4. The objective of the retaining device 210 is to retain body part 120 in a uniform position. The uniform position is important to provide a uniform thickness of the materials in body part 120. In addition, retaining device 210 also retains at least two reference materials 130 whereby the reference materials 130 being positioned for a comparative determination during a simultaneous irradiation by radiation means 110. To make the retaining device 210 also a practical device, a means for adjusting the retaining device 210 could be included to host and retain body parts 120 and the materials 130 of various sizes. FIGS. 2, 3 and 4 show different mechanisms to adjust the position of the retaining device 210. For example, wedges 220 and 230 can be used to slide along each other or a telescopic cylinders 240 can be used to telescopically extend or shorten to adjust the position.

The retaining device 210 in FIG. 1 could include a cylinder (not shown) to fit and retain the body part 120 and reference materials 130. The retaining device 210 could also include a system of two paddles 250 and 260 to fit and retain the body part 120 and reference materials 130 as shown in FIGS. 2, 3 and 4. Various different configurations and shapes could be designed to serve the same purpose of retaining and hosting of the body part 120 and reference materials 130.

The reference materials could be construed as wedges 220 and 230 as in FIG. 2. The reference materials could also be construed in cylindrical compartments 240 as shown in FIG. 3. The latter is particularly useful when liquids, such as oil and water, are used as reference materials 130. In the most general sense, the reference materials 130 could be solids and/or liquids. As mentioned above, the key idea is to select the reference materials so that the attenuation characteristics of the reference materials 130 are equivalent to the attenuation characteristics of the selected/modeled body part 120. The solid and/or liquid of the reference material could either represent a fat tissue or a glandular tissue as long as the materials are distinct enough to provide the necessary resolution to distinguish the modeled materials in the body part 130. As is shown in FIG. 2 by top view 270, the reference materials M1 and M2 could be positioned parallel to each other so that the beams 115 pass through the reference materials separately. Each wedge 220 and 230 contains both reference materials M1 and M2. In this case the attenuation values 180 are discrete. A similar parallel configuration of the reference materials M3 and M4 is shown in FIG. 3 by top view 272. Alternatively, as shown in FIG. 4 by the top view 274 the reference materials M5 and M6 could be positioned on top of each other so that the each beam 115 passes through both reference materials 130. The materials could then be made as wedges 222 and 232. In this case the attenuation values 180 provide a more continuous pattern, provided that the materials are shaped differently.

The radiating device 100 further comprises means for calculating 190 the proportion of the body materials 200 defining a body part based on the detected attenuated values 170 and 180. The calculating means could be a computer based system that is able to receive the attenuated values and calculate and determine the proportion 200 of body materials of the selected body part 120. A computer system is described for purposes of example only. An exemplary embodiment of the invention as described below to calculate the proportion 200 may be implemented in any type of computer system, programming or processing environment. The following embodiment is an example of the steps that could be included in the calculating means 190. The exemplary embodiment derives a mammographic density based on a single energy X-ray absorptiometry of the breast. The example measures the breast tissue on a pixel by pixel basis and determines the proportion 200 in terms of percentage fat. The breast in this particular example is modeled as two materials, i.e. fat and glandular tissue. It would be possible to model the breast as a three or more compartment model. Summing up all the pixels in the image detected by detector 160 results in a total fat and glandular mass which could be represented as a percentage fat mass. The subjective threshold or image interpretation would be eliminated. In addition, all the densitometric information in the image (gray scale values, color schemes, or the like) would contribute to the measure of the proportion 200, increasing the technique's power.

The following equations were derived to quantify SXA tissue density. As an exemplary embodiment of the present invention, assume that one is taking mammograms with a single energy conical x-ray source 110 using a detector 160 with film screen or direct digital detector. First define % FAT in terms of compression thickness:

$$\% \ FAT = \frac{\text{total\_fat\_mass}}{\text{total\_mass}} * 100 = \frac{\sum_{i,j=0}^{N,M} w_{f_{i,j}} a_{i,j} \rho_f}{\sum_{i,j=0}^{N,M} \left( w_{f_{i,j}} a_{i,j} \rho_f + w_{l_{i,j}} a_{i,j} \rho_l \right)} \quad (1)$$

where $w_f$ and $w_i$ are the compression thickness' of fat and lean respectively for each pixel, $\rho$ is the component density (fat and lean), ij are the subscripts denoting the rows and columns in the image, N,M are the total number of rows and columns in an image, and $a_{ij}$ is the cross sectional area of each pixel. The area for each pixel varies as a function of position due to the cone beam geometry of the device. However each pixel's cross sectional area is known explicitly by device geometry of the radiation means 110. The pixel-specific SXA equation relates the total x-ray attenuation to the attenuation of each component by:

$$I_{i,j} = I(0) e^{-(\mu_f \rho_f w_{f_{i,j}} + \mu_l \rho_l w_{l_{i,j}})} \quad (2)$$

where $\mu$=mass attenuation coefficient (cm²/g) and I(0)= Incident x-rays. In this model, W is the compression thickness and constant:

$$W = w_{f_{i,j}} + w_{l_{i,j}} \quad (3)$$

and equation (3) can be substituted into equation (2) to eliminate either the $w_f$ or $w_i$. If reference materials 130 are imaged with simultaneously with the body part (i.e. breast) 120 containing a sample 100% fat and 100% glandular tissue at the identical compression thickness W, equation (2) can be solved to find each pixel's unique $\mu\rho$ combination. For example, in the 100% fat reference, $w_i$=0 such that $$\mu_f \rho_f = \frac{-\ln\left(\frac{I'}{I(0)}\right)}{W} \quad (4)$$

where I' is transmission through fat reference of thickness W. Likewise, in the 100% lean phantom reference, $w_f=0$ and $$\mu_l \rho_l = \frac{-\ln\left(\frac{I''}{I(0)}\right)}{W} \quad (5)$$

where I" is the transmission through the lean reference of thickness W. Substituting equations (4) and (5) into (2) and solving for $w_f$ results in $$w_{f_{i,j}} = \frac{\ln\left(\frac{I_{i,j}}{I'}\right)}{\ln\left(\frac{I''}{I'}\right)} * W \quad (6)$$

and substituting this into equation (1), the % FAT equation becomes a function of pixel position, reference material values, the density ratio, and the measured attenuation at each pixel:

$$\% \ FAT = \frac{\sum_{i,j=0}^{N,M} \frac{\ln\left(\frac{I_{i,j}}{I'}\right)}{\ln\left(\frac{I''}{I'}\right)} W a_{i,j} \rho_f}{\left(\sum_{i,j=0}^{N,M} \frac{\ln\left(\frac{I_{i,j}}{I'}\right)}{\ln\left(\frac{I''}{I'}\right)} W a_{i,j} \rho_f + \left(W - \frac{\ln\left(\frac{I_{i,j}}{I'}\right)}{\ln\left(\frac{I''}{I'}\right)} W\right) a_{i,j} \rho_l\right)} * 100 = \quad (7)$$

$$\frac{\sum_{i,j=0}^{N,M} \frac{\ln\left(\frac{I_{i,j}}{I'}\right)}{\ln\left(\frac{I''}{I'}\right)} a_{i,j}}{a_{i,j}\left(\sum_{i,j=0}^{N,M} \frac{\ln\left(\frac{I_{i,j}}{I'}\right)}{\ln\left(\frac{I''}{I'}\right)} + \left(1 - \frac{\ln\left(\frac{I_{i,j}}{I'}\right)}{\ln\left(\frac{I''}{I'}\right)}\right) \frac{\rho_l}{\rho_f}\right)} * 1.00$$

This derivation is simplified to demonstrate the ideal case. Flat field corrections would have to be taken into account. The calculating means 190 could therefore also include means for correcting the attenuation values for position dependent variations of the source 110. However, the variations of the film, x-ray characteristics, developing variations, etc., are all incorporated into the attenuation values of the reference materials 130 and the body part (i.e. breast) 120. SXA will work for the breast area at the same height as the reference materials 130 measured in the same image with the breast 120. In addition, and probably in most of the cases, there might not be a complete 100% match between the reference materials 130 and the materials in the body part 120. In that case a simple ratio or correction factor could be used in the calculating means to correct for the attenuation values for the material of interest is determined.

It is important to note that while the calculating means 190 has been described in the context of a functional data processing system and method, those skilled in the art will appreciate that the mechanism of the present invention is capable of being distributed in the form of a computer readable medium of instructions in a variety of forms, and that the present invention applies equally regardless of the particular type of signal bearing medium used to actually carry out the distribution. Examples of computer readable medium include: recordable type media such as floppy disks and CD-ROMS and transmission type media such as digital and analog communication links. In addition, the present invention could be implemented and coded in different programming languages such as, but not limited to, for example C and C++ programming languages, JAVA or Java script, or DHTML.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed is:

1. An apparatus for comparatively determining a proportion of body materials defining a body part, said radiation device comprising:
    (a) at least two reference materials having attenuation characteristics, said reference materials being positioned in a uniform position for said comparative determination during a simultaneous irradiation of said body part and said reference materials, and wherein said attenuation characteristics are selected in correspondence to said body materials; and
    (b) a calculating means for calculating said proportion of said body materials defining a body part based on said comparative determination of said materials and said body part.

2. The apparatus as set forth in claim 1, wherein said body part comprises a breast and said proportion is a breast density.

3. The apparatus as set forth in claim 1, wherein said body part comprises an organ and said proportion is an organ density.

4. The apparatus as set forth in claim 1, wherein said body part comprises bone and said proportion is a bone density.

5. The apparatus as set forth in claim 1, wherein said body part comprises muscle and said proportion is a muscle density.

6. The apparatus as set forth in claim 1, wherein said body part comprises processed tissue and said proportion is a processed tissue density.

7. The apparatus as set forth in claim 1, wherein said reference materials are solids.

8. The apparatus as set forth in claim 7, wherein one of said attenuation characteristics of said reference materials is equivalent to an attenuation characteristic of a fat tissue.

9. The apparatus as set forth in claim 7, wherein one of said attenuation characteristics of said reference materials is equivalent to an attenuation characteristic of a glandular tissue.

10. The apparatus as set forth in claim 1, wherein said reference materials are liquids contained in compartments.

11. The apparatus as set forth in claim 10, wherein one of said attenuation characteristics of said reference materials is equivalent to an attenuation characteristic of a fat tissue.

12. The apparatus as set forth in claim 10, wherein one of said liquids is an oil.

13. The apparatus as set forth in claim 10, wherein one of said attenuation characteristics of said reference materials is equivalent to an attenuation characteristic of a glandular tissue.

14. The apparatus as set forth in claim 10, wherein one of said liquids is a water.

15. The apparatus as set forth in claim 1, wherein at least one of said reference materials is a solid and at least one of said reference materials is a liquid contained in a compartment.

16. The apparatus as set forth in claim 15, wherein said solid has an attenuation characteristic equivalent to a fat tissue and said liquid has an attenuation characteristic equivalent to a glandular tissue.

17. The apparatus as set forth in claim 16, wherein said liquid is a water.

18. The apparatus as set forth in claim 15, wherein said liquid has an attenuation characteristic equivalent to a fat tissue and said solid has an attenuation characteristic equivalent to a glandular tissue.

19. The apparatus as set forth in claim 18, wherein said liquid is an oil.

20. The apparatus as set forth in claim 1, wherein said reference materials are construed as blocks.

21. The apparatus as set forth in claim 1, wherein said reference materials are construed as wedges.

22. The apparatus as set forth in claim 1, wherein said reference materials are construed in cylindrical compartments.

23. The apparatus as set forth in claim 1, further comprising a device for retaining therein said body part in said uniform position.

24. The apparatus as set forth in claim 23, wherein said retaining device further comprises means for adjusting to host and retain said body part and said materials of various sizes.

25. The apparatus as set forth in claim 1, further comprising a radiation means for simultaneously irradiating said body part and said reference materials thereby creating attenuated beams of said materials and said body part.

26. The apparatus as set forth in claim 25, wherein said radiation means is a single energy X-ray absorptiometer.

27. The apparatus as set forth in claim 25, wherein said radiation means is a single photon absorptiometer.

28. The apparatus as set forth in claim 25, further comprising a detector to detect said attenuated beams as attenuated values of said materials and said body part.

29. The apparatus as set forth in claim 28, wherein said detector presents said attenuated beams in attenuation values.

30. The apparatus as set forth in claim 28, wherein said attenuation values are presented by said detector according to a color scheme.

31. The apparatus as set forth in claim 28, wherein said attenuation values are presented by said detector according to a gray scale.

32. The apparatus as set forth in claim 28, wherein said calculating means further comprises means for correcting said attenuation values for position dependent variations of said radiation means.

33. A method for comparatively determining a proportion of body materials defining a body part, said radiation device comprising:
   (a) providing at least two reference materials having attenuation characteristics, said reference materials being positioned in a uniform position for said comparative determination during a simultaneous irradiation of said body part and said reference materials, and wherein said attenuation characteristics are selected in correspondence to said body materials; and
   (b) providing a calculating means for calculating said proportion of said body materials defining a body part based on said comparative determination of said materials and said body part.

34. The method as set forth in claim 33, wherein said body part comprises a breast and said proportion is a breast density.

35. The method as set forth in claim 33, wherein said body part comprises an organ and said proportion is an organ density.

36. The method as set forth in claim 33, wherein said body part comprises bone and said proportion is a bone density.

37. The method as set forth in claim 33, wherein said body part comprises muscle and said proportion is a muscle density.

38. The method as set forth in claim 33, wherein said body part comprises processed tissue and said proportion is a processed tissue density.

39. The method as set forth in claim 33, wherein said reference materials are solids.

40. The method as set forth in claim 39, wherein one of said attenuation characteristics of said reference materials is equivalent to an attenuation characteristic of a fat tissue.

41. The method as set forth in claim 39, wherein one of said attenuation characteristics of said reference materials is equivalent to an attenuation characteristic of a glandular tissue.

42. The method as set forth in claim 33, wherein said reference materials are liquids contained in compartments.

43. The method as set forth in claim 42, wherein one of said attenuation characteristics of said reference materials is equivalent to an attenuation characteristic of a fat tissue.

44. The method as set forth in claim 42, wherein one of said liquids is an oil.

45. The method as set forth in claim 42, wherein one of said attenuation characteristics of said reference materials is equivalent to an attenuation characteristic of a glandular tissue.

46. The method as set forth in claim 42, wherein one of said liquids is a water.

47. The method as set forth in claim 33, wherein at least one of said reference materials is a solid and at least one of said reference materials is a liquid contained in a compartment.

48. The method as set forth in claim 47, wherein said solid has an attenuation characteristic equivalent to a fat tissue and said liquid has an attenuation characteristic equivalent to a glandular tissue.

49. The method as set forth in claim 48, wherein said liquid is a water.

50. The method as set forth in claim 47, wherein said liquid has an attenuation characteristic equivalent to a fat tissue and said solid has an attenuation characteristic equivalent to a glandular tissue.

51. The method as set forth in claim 50, wherein said liquid is an oil.

52. The method as set forth in claim 33, wherein said reference materials are construed as blocks.

53. The method as set forth in claim 33, wherein said reference materials are construed as wedges.

54. The method as set forth in claim 33, wherein said reference materials are construed in cylindrical compartments.

55. The method as set forth in claim 33, further comprising the step of providing a device for retaining therein said body part in said uniform position.

56. The method as set forth in claim 55, wherein said step of providing retaining device further comprises the step of providing means for adjusting to host and retain said body part and said materials of various sizes.

57. The method as set forth in claim 33, further comprising the step of providing a radiation means for simultaneously irradiating said body part and said reference materials thereby creating attenuated beams of said materials and said body part.

58. The method as set forth in claim 57, wherein said radiation means is a single energy X-ray absorptiometer.

59. The method as set forth in claim 57, wherein said radiation means is a single photon absorptiometer.

60. The method as set forth in claim 57, further comprising the step of providing a detector to detect said attenuated beams as attenuated values of said materials and said body part.

61. The method as set forth in claim 60, wherein said detector presents said attenuated beams in attenuation values.

62. The method as set forth in claim 60, wherein said attenuation values are presented by said detector according to a color scheme.

63. The method as set forth in claim 60, wherein said attenuation values are presented by said detector according to a gray scale.

64. The method as set forth in claim 60, wherein said calculating means further comprises means for correcting said attenuation values for position dependent variations of said radiation means.

65. An apparatus for comparatively determining a proportion of materials defining a part wherein said part is a human part, animal part, plant part, a processed tissue part or a homogenized tissue part, said radiation device comprising:

(a) at least two reference materials having attenuation characteristics, said reference materials being positioned in a uniform position for said comparative determination during a simultaneous irradiation of said part and said reference materials, and wherein said attenuation characteristics are selected in correspondence to said materials; and (b) a calculating means for calculating said proportion of said materials defining a part based on said comparative determination of said materials and said part.

66. A method for comparatively determining a proportion of materials defining a part wherein said part is a human part, animal part, plant part, a processed tissue part or a homogenized tissue part, said radiation device comprising:

(a) providing at least two reference materials having attenuation characteristics, said reference materials being positioned in a uniform position for said comparative determination during a simultaneous irradiation of said part and said reference materials, and wherein said attenuation characteristics are selected in correspondence to said materials; and (b) providing a calculating means for calculating said proportion of said materials defining a part based on said comparative determination of said materials and said part.

* * * * *